US009694158B2

(12) United States Patent
    Slim

(10) Patent No.: US 9,694,158 B2
(45) Date of Patent: Jul. 4, 2017

(54) TORQUE FOR INCREMENTALLY ADVANCING A CATHETER DURING RIGHT HEART CATHETERIZATION

(71) Applicant: Ahmad Mohamad Slim, San Antonio, TX (US)

(72) Inventor: Ahmad Mohamad Slim, San Antonio, TX (US)

(*) Notice: Subject to any disclaimer, the term of this patent is extended or adjusted under 35 U.S.C. 154(b) by 306 days.

(21) Appl. No.: 13/647,051

(22) Filed: Oct. 8, 2012

(65) Prior Publication Data

US 2013/0102888 A1   Apr. 25, 2013

Related U.S. Application Data

(60) Provisional application No. 61/549,893, filed on Oct. 21, 2011.

(51) Int. Cl.
| | | |
|---|---|---|
| A61B 5/05 | (2006.01) | |
| A61B 8/14 | (2006.01) | |
| A61B 5/00 | (2006.01) | |
| A61M 25/00 | (2006.01) | |
| A61B 1/00 | (2006.01) | |
| A61B 1/04 | (2006.01) | |
| A61M 25/01 | (2006.01) | |

(Continued)

(52) U.S. Cl.
    CPC ........... *A61M 25/0113* (2013.01); *A61B 6/12* (2013.01); *A61M 25/00* (2013.01); *A61M 25/0105* (2013.01); *A61M 25/09* (2013.01); *A61M 25/0905* (2013.01); *A61M 25/09041* (2013.01); *A61M 2025/09133* (2013.01)

(58) Field of Classification Search
    CPC .......... A61M 25/0105; A61M 25/0113; A61M 25/09041; A61M 25/09; A61M 25/0905; A61M 2025/09133; A61B 17/28; A61B 17/29; A61B 17/2909; A61B 17/282; A61B 17/22031; A61B 17/320092; A61B 6/12; A61B 2017/2926; B25B 9/02
    USPC ....... 600/102, 106, 114, 424, 434, 585, 117, 600/466, 131; 604/508, 510, 544, 95.01, 604/159; 606/1, 44, 51, 52, 205, 227
    See application file for complete search history.

(56) References Cited

U.S. PATENT DOCUMENTS 5,114,403 A * 5/1992 Clarke .................. A61M 25/01
                                              604/95.04
5,176,647 A * 1/1993 Knoepfler ...................... 604/158
(Continued)

*Primary Examiner* — Anhtuan T Nguyen
*Assistant Examiner* — William Chou
(74) *Attorney, Agent, or Firm* — Robert L. McRae; Gunn, Lee & Cave, P.C.

(57) ABSTRACT

A torque for controlling the advancement and rotation of a right heart catheter during a right heart catheterization procedure. The torque has a casing with a cavity for receiving a core, and a lumen for receiving the right heart catheter. A gripper is disposed within the core to tightly grip the right heart catheter. The core has a plurality of threads that engage teeth of a handle. The handle is attached to the casing at an axis and rotates about the axis during use. The core has an elongated spiraled recess which is engaged by a guide pin attached to the casing and extending within the cavity. When the handle is rotated, the teeth of the handle engage the threads to rotate the core, and the guide pin engages the elongated spiraled recess to move the core laterally, thereby advancing and rotating the right heart catheter.

12 Claims, 6 Drawing Sheets

(51) Int. Cl.
*A61M 25/09* (2006.01)
*A61B 6/12* (2006.01)

(56) References Cited

U.S. PATENT DOCUMENTS

| | | | |
|---|---|---|---|
| 6,171,234 B1* | 1/2001 | White et al. | 600/102 |
| 6,726,675 B1* | 4/2004 | Beyar | 604/510 |
| 7,326,203 B2* | 2/2008 | Papineau | A61B 17/32002 606/104 |
| 7,397,091 B2* | 7/2008 | Suenaga | 257/369 |
| 2002/0198538 A1* | 12/2002 | Kortenbach | A61B 17/122 606/139 |
| 2004/0172116 A1* | 9/2004 | Seifert | A61M 25/0097 607/119 |
| 2005/0020986 A1* | 1/2005 | Mickley et al. | 604/234 |
| 2006/0146010 A1* | 7/2006 | Schneider | 345/156 |
| 2006/0229587 A1* | 10/2006 | Beyar et al. | 604/510 |
| 2007/0191865 A1* | 8/2007 | Pappas | 606/108 |
| 2008/0045892 A1* | 2/2008 | Ferry et al. | 604/95.01 |
| 2010/0063437 A1* | 3/2010 | Nelson et al. | 604/35 |
| 2011/0178370 A1* | 7/2011 | Frassica | 600/114 |
| 2013/0090594 A1* | 4/2013 | Palmer | A61J 7/0053 604/60 |

\* cited by examiner

TORQUE FOR INCREMENTALLY ADVANCING A CATHETER DURING RIGHT HEART CATHETERIZATION

This is a utility patent application claiming priority to U.S. Provisional Patent Application No. 61/543,893, filed Oct. 6, 2011, which is expressly incorporated herein by reference.

BACKGROUND OF THE INVENTION

1. Field of the Invention

The present invention relates to heart catheterization procedures, and more specifically to right heart catheterization procedures. The present invention provides a torque for use in right heart catheterization procedures to apply rotational force to a right heart catheter to incrementally advance the right heart catheter through the arteries and valves of the heart during a right heart catheterization procedure. The torque of the present invention provides incremental advancement of the right heart catheter, which allows a physician to have more control over the movement of the right heart catheter over manual rotation and advancement by the physician, as is currently practiced.

2. Description of the Related Art

Right heart catheterization is a medical procedure commonly used to evaluate the blood pressure in the right side of a patient's heart and in his or her lungs. The procedure allows a physician to diagnose or evaluate the existence or progression of various conditions such as pulmonary hypertension, heart failure, congenital heart failure, valveular heart disease/malfunction or cardiomyopathy.

Right heart catheterization typically involves inserting a right heart catheter into the iliac vein of a patient and manually rotating and pushing the right heart catheter through the venous system while monitoring the location of the catheter using fluoroscopic x-ray. The right heart catheter is manually guided by the physician through the inferior vena cava into the right atrium of the patient's heart. From there, the physician continues to manually advance the right heart catheter through the tricuspid valve into the right ventricle, and on through the pulmonary valve into the pulmonary artery.

The catheter is attached to one or more hemodynamic monitors known in the art of right heart catheterization to take several pressures during the procedure. For instance, once the right heart catheter enters the right atrium, the right atrium pressure is recorded. As the right heart catheter is positioned through the tricuspid valve and into the right ventricle, the right ventricular pressure is obtained. As the catheter passes through the pulmonary valve into the pulmonary artery, the mean pulmonary pressure in the pulmonary trunk is obtained. Finally, once the right heart catheter is positioned in the pulmonary artery, the catheter is inflated to seal the capillaries in the lungs and the capillary wedge pressure is obtained.

The manual manipulation of the right heart catheter through the right heart and arteries is guided by fluoroscopic x-ray. In the majority of right heart catheterizations, access is obtained through the iliac vein and the right heart catheter, which is a curved and flexible balloon device known and typically used by one of ordinary skill in the art of right heart catheterization, travels against its curvature through the inferior vena cava, to reach the right atrium. Once in the right atrium, the right heart catheter has to be turned clockwise externally to aim towards the tricuspid valve, which is challenging when done manually. Once the right heart catheter passes through the tricuspid valve, it is manually turned upward towards the right ventricular track and then advanced into the pulmonary artery. All of this manual maneuvering of the right heart catheter is challenging and often requires prolonged exposure to fluoroscopy with associated radiation due to the need to use fluoroscopic x-ray to monitor the positioning of the right heart catheter. The prolonged exposure to radiation is problematic in today's medical climate, as physicians are looking for ways to decrease exposure of their patients to radiation.

SUMMARY OF THE INVENTION

The present invention provides an external torque device for use with a right heart catheter to allow more controlled manipulation of the right heart catheter over manual manipulation. The enhanced control of manipulation provided by the torque of the present invention allows the physician to advance the right heart catheter through (a) the tricuspid valve and (b) the pulmonary artery more efficiently, thus minimalizing the patient's exposure to radiation. Operation of the torque of the present invention provides spiral motion with forward advancement of the right heart catheter.

The torque of the present invention comprises a hinged casing that receives and houses a core having a predefined interior lumen, generally between five to twelve French. A gripping apparatus is disposed within a first end of the core and has a predefined lumen of the same size of the predefined lumen of the core to receive a distal end of the right heart catheter. The casing comprises a first member and a second member hingedly attached to one another along end portions thereof. The first member and second member each have recesses which, when the casing is closed, define a cavity for receiving the core.

The hinges of the casing allow the casing to be opened by separating the first member and the second member along their ends opposite the hinges. Once open, the core can be removed or placed in the cavity. The torque of the present invention may provide multiple interchangeable cores having lumens of different predefined inner diameters varying from five French to twelve French to accommodate different sizes of right heart catheters. Each interchangeable core will have a corresponding gripper therein with a lumen of the same size as the lumen in the core.

Once the desired core with the desired gripper is inserted into the torque, the right heart catheter is inserted within the core and the gripper, and the casing is locked over the right heart catheter such that the right heart catheter extends through the torque of the present invention at approximately the longitudinal midline thereof. A handle is disposed along a top side of the casing between the first member and the second member, and is attached at an axis thereto to allow the handle to rotate with respect to the casing. The handle extends within the cavity, terminating in a plurality of teeth.

A portion of the outer circumference of the core has predefined threads which engage the plurality of teeth of the handle. The engagement of the plurality of teeth with the threads defines a gear similar to a worm-type gear. The core is longitudinally shorter than the cavity to allow the core to move laterally back and forth within the cavity as the handle is operated to advance the right heart catheter. An elongated substantially spiraled recess is located behind the predefined threads on the outer surface of the core and extends substantially the length between the end of the core opposite the threads and the threads. A guide pin is attached to either the first or second member of the casing, and engages the recess to guide the lateral spiral movement of the core during operation of the torque.

In operation, once the right heart catheter is manually manipulated into the right atrium and is positioned to pass through the tricuspid valve, the torque of the present invention is attached to the right heart catheter. The operator of the torque controls the advancement of the right heart catheter through the tricuspid valve by operating the handle to rotate about it's axis with respect to the casing. As the handle is operated, the teeth of the handle move along the corresponding threads of the core, which rotates the core while the guide pin within the elongated recess moves the core laterally within the cavity. This movement by the core advances the right heart catheter in spiral motion corresponding to the rotation of the core, and provides the necessary rotation and advancement of the right heart catheter through the tricuspid valve and into the right ventricle. Once in the right ventricle, the operator positions the right heart catheter upward into a position to advance through the pulmonary valve into the pulmonary artery. Further operation of the torque provides the necessary rotation and advancement of the right heart catheter through the pulmonary valve and into the pulmonary artery.

DETAILED DESCRIPTION OF THE INVENTION

Figure 1:
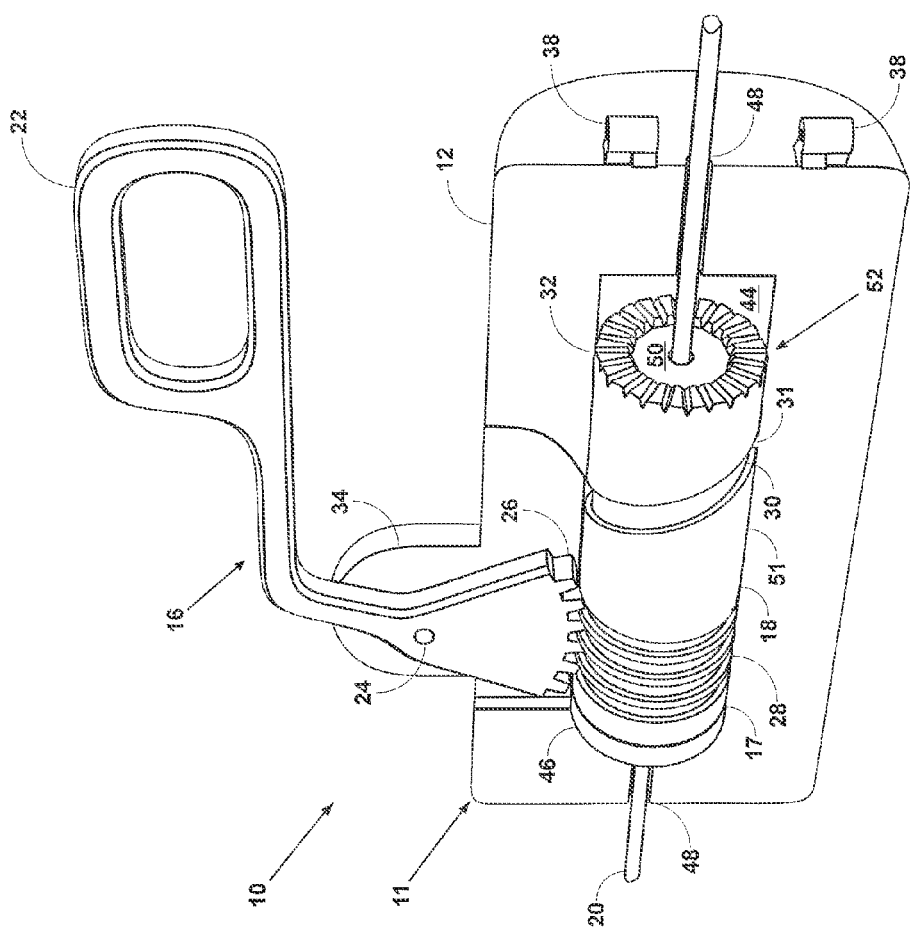
FIG. 1 is a perspective sectional view of the torque of the present invention showing the core within the cavity of the casing.
Figure 2:
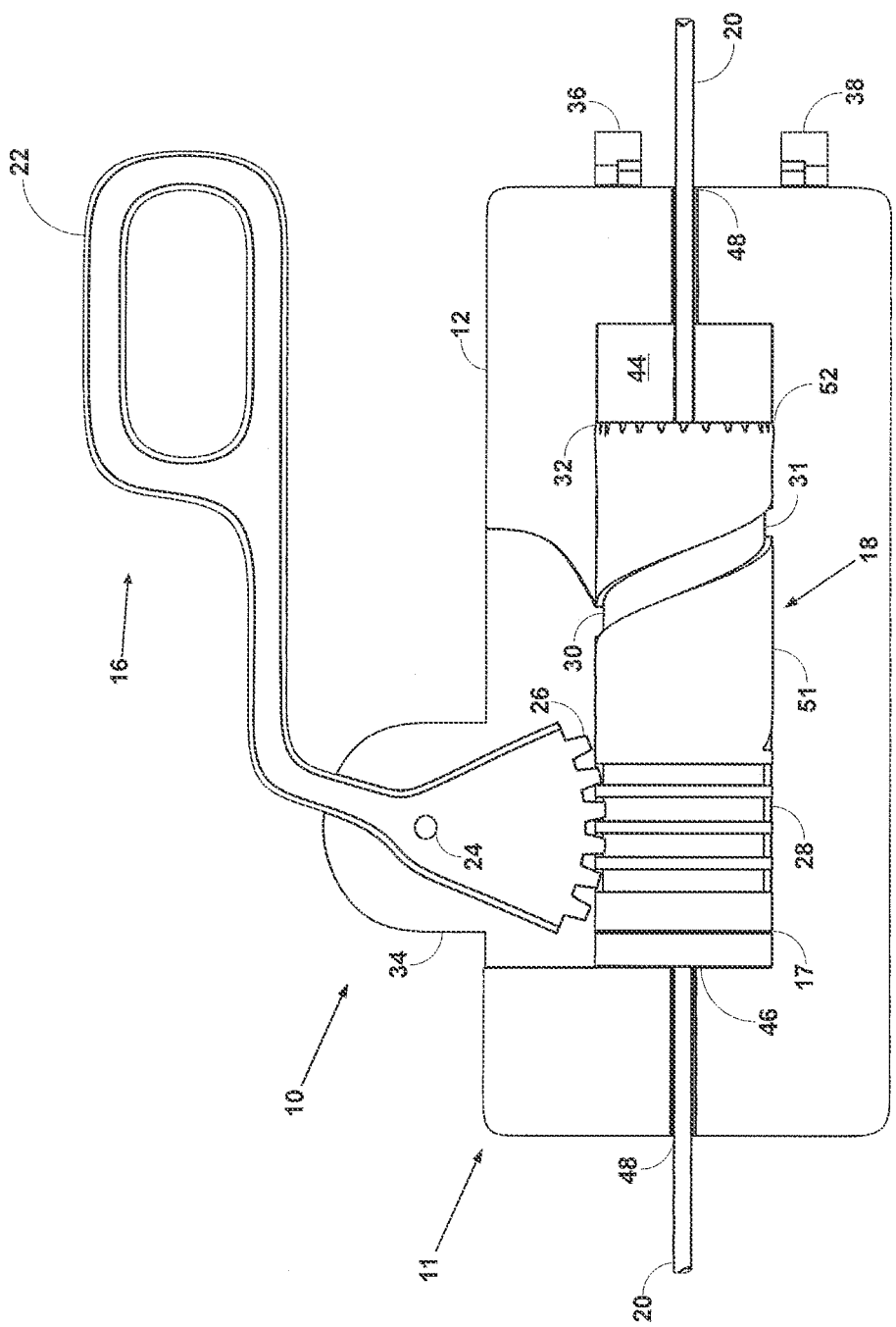
FIG. 2 is a side sectional view of the torque of the present invention showing the core within the cavity of the casing.
Figure 3:
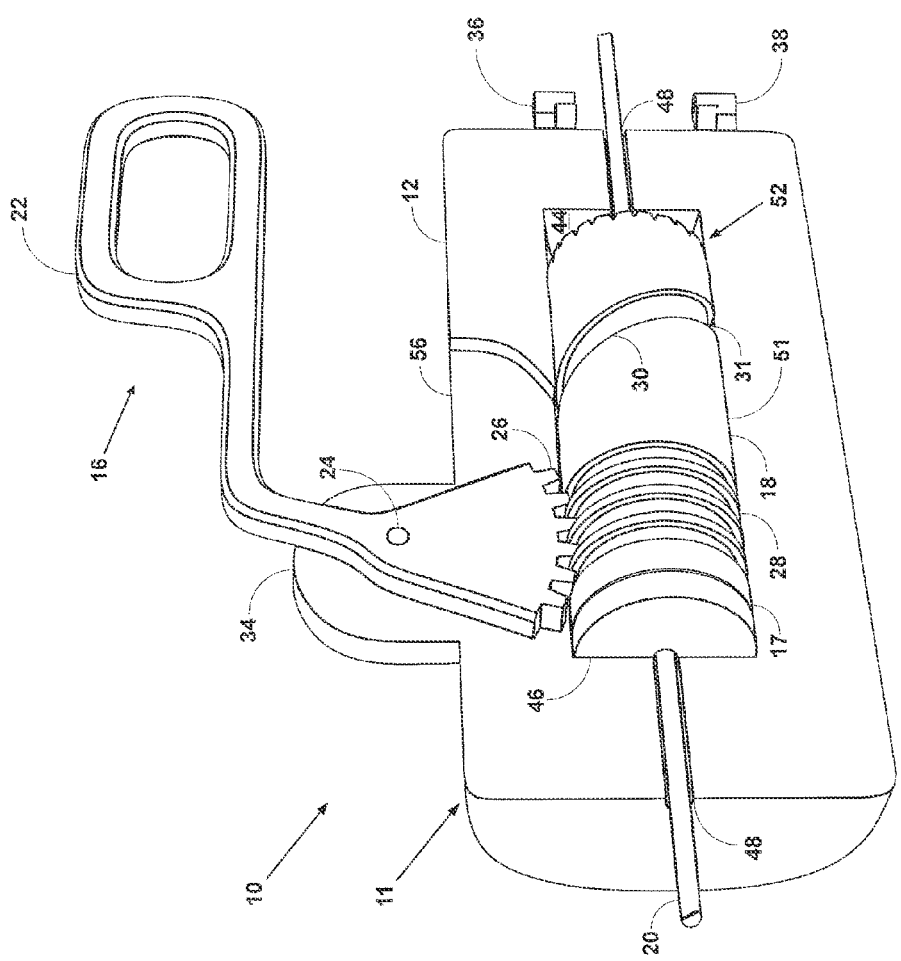
FIG. 3 is a perspective sectional view of the torque of the present invention showing the core within the cavity of the casing.
Figure 4:
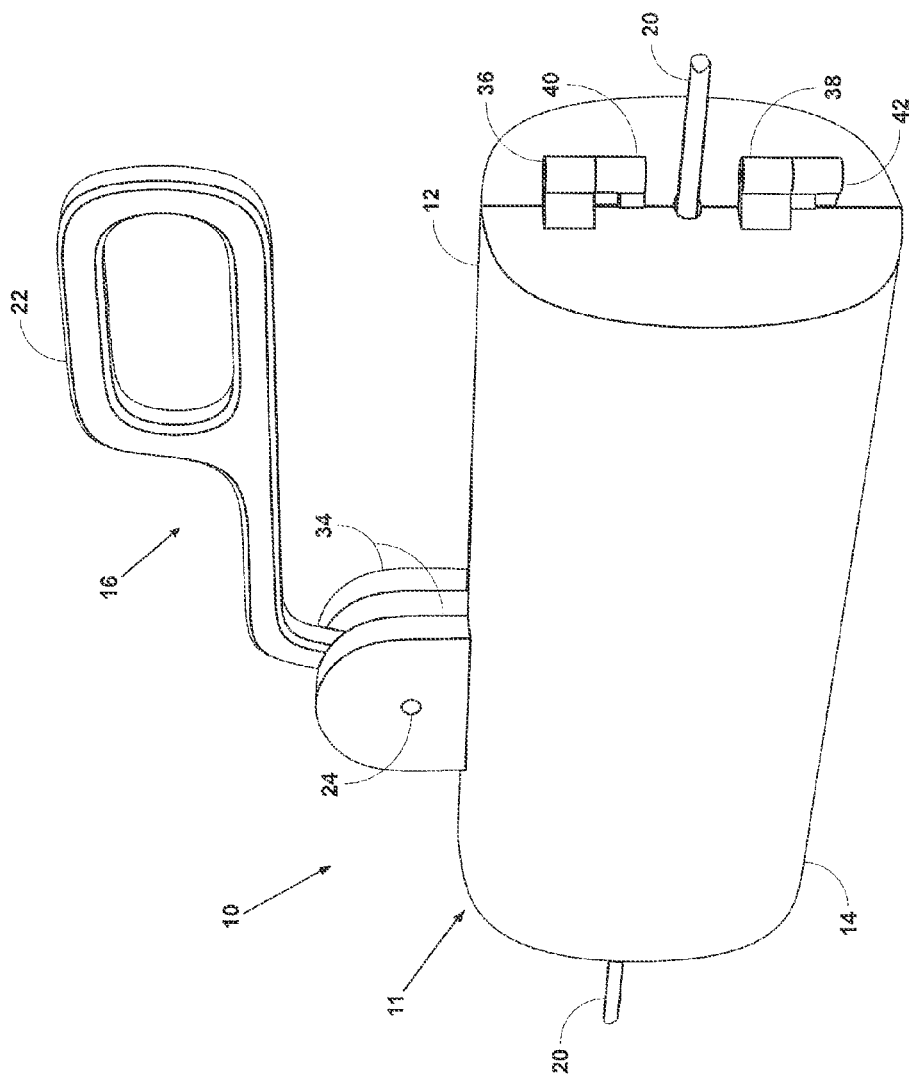
FIG. 4 is a perspective view of the torque of the present invention.

Referring to FIGS. 1 through 5, the torque 10 of the present invention is disclosed. Referring to FIGS. 1 and 4, the torque 10 comprises a casing 11. The casing 11 comprises a first member 12 and a second member 14. First member 12 and second member 14 substantially mirror each other and are opposed in orientation to one another. First member 12 comprises a recess 51, and second member 14 comprises a corresponding recess (not shown), together of which define a cavity 52 for receiving a core 18. Referring to FIGS. 1 and 2, the core 18 of the present invention is substantially cylindrically shaped, and is shorter in length than the cavity 52, which provides a space 44 within the cavity 52 to allow lateral movement of the core 18 during operation of the torque 10.

Referring to FIGS. 1, 2 and 3, the core 18 is substantially cylindrically shaped, and has a predefined lumen 50 to receive a right heart catheter 20. The lumen 50 of the present invention is of an appropriate diameter to snugly receive the right heart catheter 20. The lumen 50 of the present invention is of a diameter between five French and twelve French, and more preferably between five French and nine French. The term "French" as used herein means the unit of measurement commonly known to those of ordinary skill in the art of right heart catheterization.

The outer circumference of the core 18 comprises an elongated spiraled recess 30. A guide pin 31 is attached to the first member 12 or the second member 14 of the casing 11 and extends within the elongated spiraled recess 30 to engage the core 18. The outer circumference of the core 18 further comprises a plurality of threads 28 disposed along a first end 17 of the core 18 and extending toward a second end 32 of the core 18, terminating prior to the elongated spiraled recess 30. The elongated spiraled recess 30 extends substantially from the threads 28, but slightly spaced therefrom, toward the second end 32 of the core 18, and terminating prior thereto.

Figure 5:
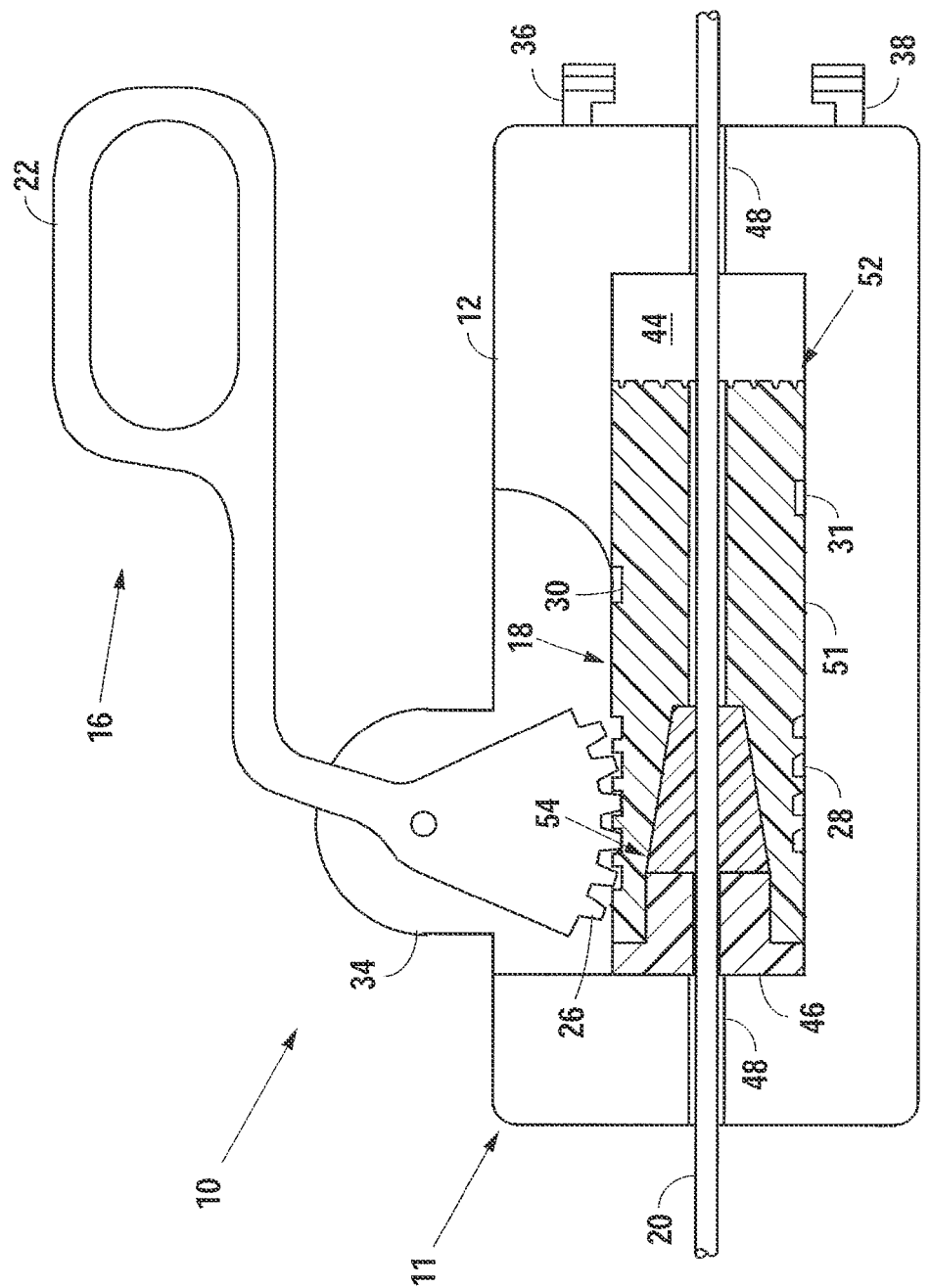
FIG. 5 is a side sectional view of the torque of the present invention.

Referring to FIG. 5, the core 18 of the present invention further comprises a gripper 54, which is substantially cone shaped. The gripper 54 has a predefined lumen which is the same size as the predefined lumen 50. The gripper 54 is disposed within the core 18 toward first end 17 and is retained therein by a retaining cap 46. The retaining cap 46 is securely attached to first end 17 of the core 18. The gripper 54 is made of a material suitable to tightly grip the right heart catheter 20 to prevent lateral sliding of the catheter 20 with respect to the core 18. Alternatively, the entire core 18 may be made of material suitable to tightly grip the right heart catheter 20, thus eliminating the need for a separate gripper 54 to be disposed within the core 18.

Referring to FIGS. 1, 2, 3 and 4, first member 12 and second member 14 comprise corresponding mounts 34. A handle 16 is disposed between first member 12 and second member 14 and is attached thereto at an axis 24. The handle 16 is attached to first member 12 and second member 14 with a pin (not shown) or other similar attaching device to provide rotational movement of the handle 16 with respect to the first member 12 and second member 14 at the axis 24. The handle 16 extends outward and backward from the mounts 34, exteriorly from first member 12 and second member 14, terminating in a grip 22. During operation, grip 22 is the portion of the handle 16 utilized by the person operating the torque 10.

First member 12 and second member 14 each have a receiving recess 56 adjacent mounts 34 for receiving the handle 16. The handle 16 extends between recesses 56 and terminates in a plurality of substantially equally spaced teeth 26. The teeth are disposed within and engage the threads 28 of the core 18. First member 12 and second member 14 have catheter receiving recesses adjacent first end 17 and second end 32 of core 18, defining a lumen 48 in the casing 11 for receiving the right heart catheter 20. First member 12 comprises a first hinge member 36 which mates with first hinge member 40 of second member 14. First member 12 also comprises a second hinge member 38 which mates with second hinge member 42 of the second member 14. Hinge members 36, 40, 38 and 42 hingedly attach first member 12 and second member 14 to comprise casing 11. As shown, hinge members 36, 40, 38 and 42 are disposed along end portions of first member 12 and second member 14, respectively. However, other locations along first member 12 and second member 14 of the respective hinge members 36, 40, 38 and 42 are possible. Along the ends of first member 12 and second member 14 opposite hinge members 36, 40, 38 and 42 is at least one latch mechanism (not shown) to latch the casing 11 after the core 18 is placed within the cavity 52, and attached to the right heart catheter 20.

Figure 7:
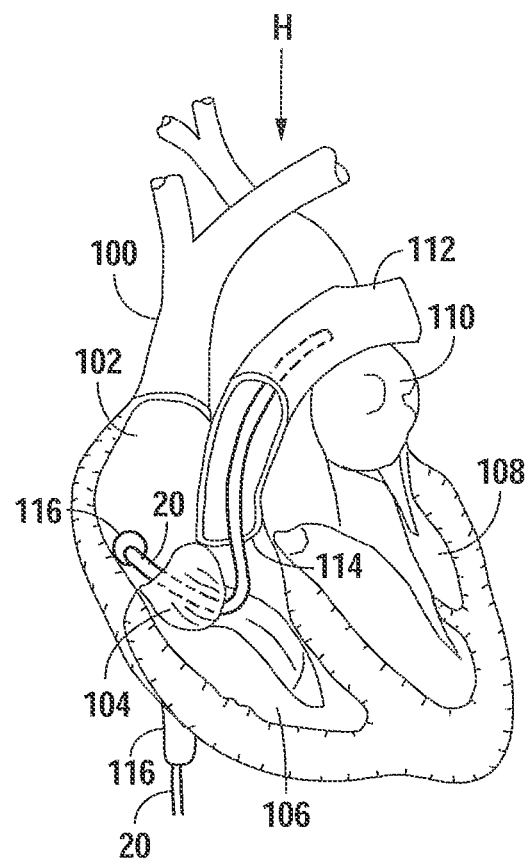
FIG. 7 is a sectional front view of a heart of the patient showing the right heart catheter advancing through the right heart of the patient.

The torque 10 of the present invention is designed to efficiently control advancement of the right heart catheter 20 through both (a) the tricuspid valve 104 and into the right ventricle 106 and (b) the pulmonary valve 114 and into the pulmonary artery 112 (see FIG. 7). Therefore, the torque 10 should be calibrated accurately to control the degree of rotation and forward advancement of the right heart catheter 20.

The length of the core 18 is sufficiently less than the length of the cavity 52 to allow lateral movement of the core 18 within the cavity 52. With the gripper 54 securely gripping the right heart catheter 20, the forward advancement of the right heart catheter 20 is directly proportional to the forward advancement of the core 18 within the cavity 52. The amount of lateral movement of the core 18 within the cavity 52 is controlled by the guide pin 31 interacting with the elongated spiraled recess 30. As the core 18 rotates by operation of the handle 16, the guide pin 31 slides within the elongated spiraled recess 30, thereby laterally sliding the core 18 within the cavity 52. The elongated spiraled recess 30 in one embodiment is configured about the circumference of the core 18 to allow approximately one centimeter of lateral movement. However, the elongated spiraled recess 30 may be configured about the circumference of the core 18 to allow greater or less lateral movement of the core 18, and consequently the right heart catheter 20.

The desired rotation or torque of the right heart catheter 20 is directly related to the rotation of the core 18. The teeth 26 of the handle 16 are disposed within and interact with the threads 28 of the core 18, and form a gear assembly similar to a worm-type gear. As the handle 16 is operated by moving the grip 22, the teeth 26 slide within the threads 28 to rotate the core 18, and consequently the right heart catheter 20. However, due to the simultaneous lateral movement of the core 18, it should be understood that not all of the teeth 26 engage the threads 28 at any given point of location of the handle 16 during operation.

Figure 6:
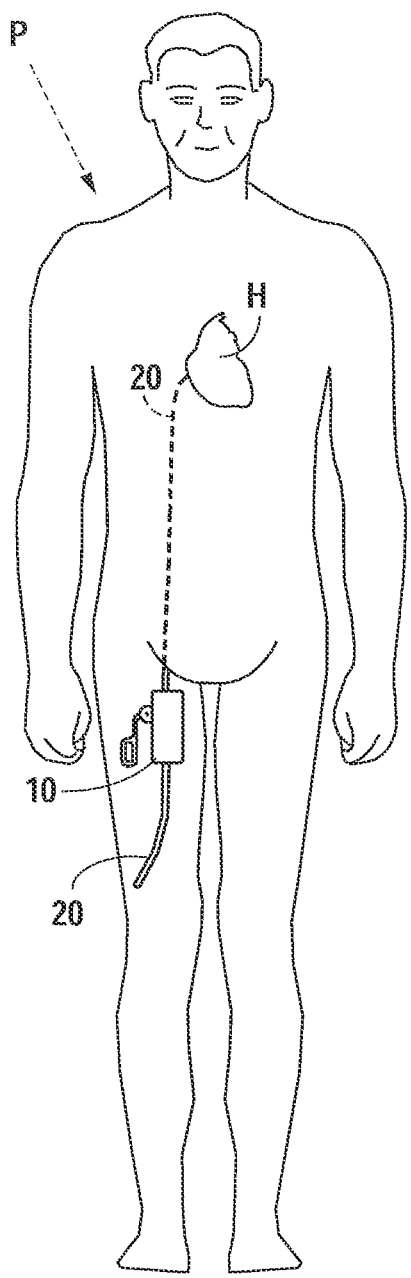
FIG. 6 is a front view of a patient undergoing a right heart catheterization with the torque of the present invention attached to the right heart catheter.

Referring to FIG. 6 and FIG. 7, in a right heart catheterization procedure using the torque 10 of the present invention, the operator (not shown), who is typically a physician of ordinary skill in the art of right heart catheterization, inserts a right heart catheter 20 into the iliac vein (not shown) of a patient P, and manually advances the right heart catheter 20 from the iliac vein into the inferior vena cava 116. The operator then manually advances the right heart catheter 20 to enter the heart H of the patient P through the right atrium 102 of the heart H, and positions the right heart catheter 20 to the tricuspid valve 104.

Once the right heart catheter 20 is at the desired location in the right atrium 102 prior to entering the tricuspid valve 104, the operator attaches the torque 10 to the right heart catheter 20 such that the right heart catheter 20 is secured within the lumen 50 and gripper 54 of the core 18, and extending through the lumen 48 of the casing 11. The operator then moves the handle by moving the grip 22 in a direction to rotate the core 18 in a clockwise rotation, thereby advancing the right heart catheter through the tricuspid valve 104 and into the right ventricle 106. The operator then manually repositions the right heart catheter 20 upward toward the pulmonary valve 114. After this manual repositioning, the grip 22 of the torque 10 is again operated to rotate the core 18 in a clockwise rotation to advance the right heart catheter 20 through the pulmonary vein 114 and into the pulmonary artery 112.

Although the invention has been described with reference to specific embodiments, this description is not meant to be construed in a limited sense. Various modifications of the disclosed embodiments, as well as alternative embodiments of the invention will become apparent to persons skilled in the art upon the reference to the description of the invention. It is contemplated that the appended claims will cover modifications and alternative embodiments that fall within the scope of the invention.

I claim:

1. A right heart catheter and torque for advancing said right heart catheter within the vascular system of a patient during a right heart catheterization comprising:
    a casing defining a cavity therein, said casing comprising at least one lumen and a guide pin attached to said casing and disposed within said cavity;
    a core disposed within said cavity of said casing, said core comprising a lumen in communication with said at least one lumen of said casing, a plurality of threads disposed along an outer circumference of said core and a spiraled recess disposed along said outer circumference of said core;
    a gripper disposed within a first end of said core, said gripper comprising a lumen corresponding to and in communication with said lumen of said core and said at least one lumen of said casing, said gripper receiving within said lumen of said gripper said right heart catheter, and tightly gripping said right heart catheter;
    a retaining cap adjacent said gripper and attached to said first end of said core, said retaining cap comprising a lumen in communication with said lumen of said gripper;
    a handle attached to said casing at an axis and rotatable about said axis, said handle comprising a grip extending outward from and external to said casing, and a plurality of teeth extending within said casing and engaging with said plurality of threads;
    wherein said guide pin of said casing extends within and engages said spiraled recess of said core; and
    wherein said core is rotatable and laterally moveable within said cavity when said handle is rotated about said axis.

2. The right heart catheter and torque as disclosed in claim 1 wherein said teeth engage said threads to rotate said core when said handle is rotated about said axis, and said guide pin engages said spiraled recess to move said core laterally within said cavity when said handle is rotated about said axis.

3. The right heart catheter and torque as disclosed in claim 1 wherein said plurality of threads are disposed along a first portion of said outer circumference of said core, said first portion being adjacent said first end of said core, and said spiraled recess is disposed along a second portion of said outer circumference, said second portion being adjacent said first portion.

4. The right heart catheter and torque as disclosed in claim 1 wherein said at least one lumen of said casing comprises a first lumen disposed within a first end of said casing and a second lumen corresponding to said first lumen disposed within a second end of said casing; said first lumen and said second lumen of said casing communicating with said lumen of said core.

5. The right heart catheter and torque as disclosed in claim 1 wherein said casing further comprises a first member and a second member hingedly attached to said first member.

6. The right heart catheter and torque as disclosed in claim 5 wherein said first member and said second member comprise corresponding recesses and corresponding mounts adjacent said corresponding recesses for receiving said handle.

7. A right heart catheter and torque for maneuvering said right heart catheter through the valves and arteries of a heart comprising:

a casing comprising a first member and a second member hingedly attached to said first member, said casing comprising a cavity, a lumen in communication with said cavity and extending through said casing, and a guide pin attached to said casing and disposed within said cavity;

a handle attached to said casing between said first member and said second member at an axis and rotatable about said axis, said handle comprising a grip extending outward from and external to said casing, and a plurality of teeth extending within said casing;

a plurality of cores, each of said plurality of cores being insertable within said cavity of said casing, rotatable and laterally slidable within said cavity, and removable from said casing;

wherein each of said plurality of cores comprises a lumen corresponding to said lumen of said casing, a gripper disposed within said core, said gripper comprising a lumen corresponding to and in communication with said lumen of said core and said at least one lumen of said casing, said gripper receiving within said lumen of said gripper said right heart catheter, and tightly gripping said right heart catheter;

a plurality of threads disposed along an outer circumference of said core and a spiraled recess disposed along said outer circumference of said core;

a retaining cap adjacent said gripper and attached to said first end of said core, said retaining cap comprising a lumen in communication with said lumen of said gripper;

wherein said guide pin of said casing extends within and engages said spiraled recess of each of said plurality of cores and slides each of said plurality of cores laterally when each of said plurality of cores is inserted within said cavity; and wherein said teeth of said handle extend within and engage said plurality of threads to rotate each of said plurality of cores when each of said plurality of cores is inserted within said cavity of said casing.

8. The right heart catheter and torque as disclosed in claim 7 wherein said teeth of said handle engage said threads of each of said plurality of said cores to rotate said core when said handle is rotated about said axis, and said guide pin engages said spiraled recesses of each of said plurality of cores to move said core laterally within said cavity when said handle is rotated about said axis when each of said plurality of cores is inserted into said cavity of said casing.

9. The right heart catheter and torque as disclosed in claim 8 wherein said plurality of threads of each of said plurality of cores are disposed along a first portion of said outer circumference of said core, said first portion, and said spiraled recess of each of said plurality of cores is disposed along a second portion of said outer circumference, said second portion being adjacent said first portion.

10. The right heart catheter and torque as disclosed in claim 9 wherein each lumen of each of said plurality of cores is a different diameter than the lumens of each of the other of said plurality of cores.

11. The right heart catheter and torque as disclosed in claim 10 wherein said first member and said second member of said casing comprise corresponding recesses and corresponding mounts adjacent said corresponding recesses for receiving said handle.

12. The right heart catheter and torque as disclosed in claim 11 wherein each lumen of said plurality of cores communicates with said lumen of said casing.

* * * * *